(12) United States Patent
Longoni

(10) Patent No.: US 7,174,903 B2
(45) Date of Patent: Feb. 13, 2007

(54) DENTAL FLOSS AND MANUFACTURING METHOD THEREOF

(75) Inventor: Elena Longoni, Trieste (IT)

(73) Assignee: Profimed S.r.l., Milan (IT)

( * ) Notice: Subject to any disclaimer, the term of this patent is extended or adjusted under 35 U.S.C. 154(b) by 66 days.

(21) Appl. No.: 10/962,546

(22) Filed: Oct. 13, 2004

(65) Prior Publication Data

US 2005/0257807 A1 Nov. 24, 2005

(51) Int. Cl.
*A61C 15/00* (2006.01)
(52) U.S. Cl. .................................... 132/321
(58) Field of Classification Search .......... 132/321; 428/362, 400
See application file for complete search history.

(56) References Cited

U.S. PATENT DOCUMENTS

| 4,142,538 | A | * | 3/1979 | Thornton | 132/321 |
| 4,198,459 | A | * | 4/1980 | Brumlik | 442/189 |
| 4,996,056 | A | * | 2/1991 | Blass | 424/443 |
| 5,526,831 | A | * | 6/1996 | Gilligan et al. | 132/321 |
| 5,711,935 | A | * | 1/1998 | Hill et al. | 424/49 |
| 5,842,489 | A | * | 12/1998 | Suhonen et al. | 132/321 |
| 6,016,816 | A | * | 1/2000 | Ariagno | 132/321 |
| 6,767,498 | B1 | * | 7/2004 | Talley et al. | 264/474 |

* cited by examiner

*Primary Examiner*—Todd E. Manahan
*Assistant Examiner*—Rachel A. Running
(74) *Attorney, Agent, or Firm*—Young & Thompson

(57) ABSTRACT

An improved dental floss and a manufacturing method thereof is disclosed, comprising a plurality of threads, preferably consisting of POY polyester filaments, which are texturized, twisted at a density ranging between 60 and 120 twists/meter, and entangled without adding binding agents.

14 Claims, No Drawings

DENTAL FLOSS AND MANUFACTURING METHOD THEREOF

BACKGROUND OF THE INVENTION

The present invention relates to a dental floss.

DESCRIPTION OF THE RELATED ART

As known, the market offers a great variety of dental flosses. A dental floss typically consists of a series of synthetic filaments, mutually coupled to form a single thread, which is then possibly imbibed with flavours and other medical substances and possibly coated with protective and binding wax.

Depending on monofilament size, count, number and material, the thread can have extremely diverse properties. Each thread has its own peculiarities, but also some disadvantages, and it is not always easy to find the most suitable compromise choice.

For example, by increasing the number of monofilaments, thread strength is increased, but elasticity is negatively affected and section diameter increases, resulting in risk of injuries to the gums and problems are encountered in manoeuvring the dental floss between the tighter interdental spaces. On the other hand, if the floss is too thin, it may tear and does not have adequate cleaning capabilities in all circumstances.

Another disadvantage which affects the dental floss of the prior art concerns its bulking during use. Normally, prior art threads are consolidated and section-tied by applying binding chemical agents which prevent—at least before use—the undesired swelling of the thread, making it difficult to insert it in the interdental spaces. These binding agents are compounded so as to dissolve upon contact with saliva, freeing the floss, which is then able to swell during use boosting its cleaning capabilities. However, these binding agents, which are necessary to maintain a minimum diameter in prior art threads, do not always behave in the desired way, since the quality and quantity of saliva with which they come into contact may vary significantly from individual to individual.

SUMMARY OF THE INVENTION

It is hence an object of the present invention to provide an improved dental floss which has excellent mechanical and physical properties in all conditions. In particular it is intended to provide a dental floss which is sufficiently compact before use—hence also being thin enough to pass through interdental spaces—and which at the same time is sufficiently elastic and bulky during use to perform the desired cleaning action without damaging the gums.

DESCRIPTION OF A CURRENTLY PREFERRED EMBODIMENT

Such objects are achieved by means of a dental floss as disclosed below. The detailed features and the advantages of the dental floss according to the invention will in any case become more apparent from the following description of a preferred embodiment of the same, given by way of a non-limiting example.

The dental floss of the invention is assembled from a basic raw material in the form of POY (pre-oriented yarn) polyester filaments.

These filaments are assembled to give a thread with 150/47 dtex value. The thread thus obtained is then texturized with techniques which are known per se.

After this, the ends of 8 threads of this type are joined, twisting them together at a density of 80 twists/meter.

This value is particularly preferred to give sufficient compactedness to the thread, without it being excessively rigid and especially being still capable of bulking according to what will be detailed in the following. In any case, a useful range varies from 60 to 120 twists/meter.

Following the twisting, the filaments are entangled, preferably mechanically, to give sufficient body and to limit bulkiness and section at rest of the finished thread.

Unlike many solutions offered by the prior art, no binding, agglomerating or strengthening agent is added to the semi-finished product thus obtained. As a matter of fact, thanks to the shrewd choice of material, composition and processing, the dental floss of the invention has been shown to be able to maintain a correct body without the need to add further chemical agents, which would represent additional costs and would not allow to obtain the desired swelling during use.

Finally, finishing operations may be performed, such as for example addition of a flavour and/or wax coating.

Flavouring is performed applying a cold process, with natural flavours known per se.

Wax coating can employ microcrystalline or natural waxes which account for about 2–10% of the thread weight. For example, a wax coating may be applied to the floss by known techniques of drawing the floss through the hot mixture which may be microcrystalline wax or possibly blanched natural bee's wax.

Following the wax coating, in the manufacturing phase the thread continues its journey along an artificially elongated path, to allow cooling of the wax, and is then wound on a large storing bobbin.

Finally, a series of small spools can be obtained from the large bobbin to be introduced in a dental floss dispenser to be sold to the public, for example the container/dispenser described in the Italian application MI2004U/168 in the name of the same Applicant.

The dental floss thus obtained has excellent physical and mechanical features.

In particular, tests have shown that the final value, in the 1200–1400 dtex range, is the best compromise choice, as it still allows smooth penetration even between the tightest interdental spaces, but is sufficiently bulky both to remove possible food particles on both sides of the teeth with which it comes into contact, and to disturb the plaque-forming process and hence to prevent plaque proliferation.

The final number of 376 filaments allows a sufficiently bulked product, which guarantees good retention of the finishing products that may be applied, in particular waxes and/or flavours, which are effectively trapped between the various filaments. Said value has also been shown to be within an ideal range of 280–400 filaments, which is the one best guaranteeing sufficient elasticity to avoid gum traumas, but at the same time also displaying good capability to remove food particles, plaque and impurities from the teeth.

The choice of polyester as filament material guarantees optimal qualities of resistance to traction and to friction. Moreover, since it has a low hygroscopic value, it is not subject to major behaviour changes even after prolonged exposure to water or saliva.

Finally, the design illustrated, in which twisting and entangling of the filaments, but absence of any chemical binding agent is provided, achieves an advantageous behaviour during use. As a matter of fact, on the one hand it is possible to guarantee the necessary initial compactedness of the floss for easy insertion and gliding between interdental spaces; on the other hand, after some friction of the dental floss on the teeth, the entangling is progressively dissolved, which causes the floss to progressively increase in bulkiness, so that its cleaning capacity becomes more efficient without, however, being dangerous for linings and gums.

COMPARISON EXAMPLES AND TRIALS

The dental floss of the invention, by increasing its during use and, specifically, when it is subject to a mechanical stress, allows for better removal of interdental plaque and helps reduce gingival bleeding.

The supposed effectiveness of the dental floss of the invention has been verified by comparing it with three of the most widespread and most widely marketed types of dental floss.

The trial involved 40 patients divided in 4 groups. The first group used a waxed dental floss, with the following technical features: Regular, PA 6.6, Dtex 940/136 (referred to in the following as "regular waxed" dental floss). The second group used a monofilament dental floss, with the following technical features: PTFE, Dtex 1200, folded, slightly waxed (referred to in the following as "ptfe slightly waxed" floss). The third group used a thin dental floss, with the following technical features: Fine, PA 6.6, Dtex 700/104 (referred to in the following as "fine non-waxed" floss). Finally, the fourth group used the floss of the invention (referred to in the following as "Riser™" floss), with the following technical features: PL, Dtex 1300/376.

The following periodontal indexes were recorded at the beginning and at the end of the trial on each patient:

1. the bacterial plaque index, applying the O'LEARY (PCR) technique, using a 2-colour plaque revealer;
2. the bleeding score, applying the (GBI) AIMANO and BAY technique.

The patients received no professional oral hygiene care, but were only instructed on oral hygiene techniques and were not informed about the type of dental floss used.

The results are illustrated in the following tables, where table 1 shows the values of the PCR and GBI parameters in two successive moments of the trial, while table 2 shows the average reduction percentage of the indexes as they were recorded in the patients.

TABLE 1

| Type of floss | PCR1 | PCR2 | GBI1 | GBI2 |
|---|---|---|---|---|
| Fine non-waxed | 38.09% | 19.24% | 24.66% | 16.82% |
| Ptfe slightly waxed | 53.17% | 29.79% | 39.03% | 29.24% |
| Regular waxed | 41.60% | 19.90% | 31.80% | 15.97% |
| Riser ™ | 53.49 | 16.12% | 18.49% | 9.13% |

TABLE 2

| Type of floss | PCR | GBI |
|---|---|---|
| Fine non-waxed | 49.49% | 31.79% |
| Ptfe slightly waxed | 43.97% | 25.08% |
| Regular waxed | 52.16% | 49.78% |
| Riser ™ | 69.86 | 50.62% |

The differences among the different groups are relevant, in particular as far as the plaque index is concerned: use of the floss of the invention has allowed an average reduction by about 70%, which is noticeably more than the other dental flosses. In particular, the dental floss of the invention has proved much more effective than the other flosses in removing interdental plaque in those patients who have a moderate to severe periodontitis.

The average reduction of the plaque index achieved by the floss of the invention is higher than that of the other dental flosses by 43.92%. The average reduction of the bleeding index achieved by the Riser floss is higher than that of the other dental flosses by 42.39%.

It is understood, however, that the invention is not limited to the specific embodiment illustrated above, which represents only a non-limiting example of the scope of the invention, but that a number of changes may be made, all within the reach of a skilled person in the field, without departing from the scope of the invention as defined in the accompanying claims.

The invention claimed is:

1. Dental floss comprising:
    a floss element comprising from 6 to 10 mutually twisted threads, the threads each consisting of texturized POY filaments, the filaments twisted so as to obtain a cohesion effect and entangled filaments,
    the floss element being free of any binding agents,
    wherein said floss element comprises a total number of filaments ranging between 280 and 400,
    wherein each of said plurality of threads comprises 47 filaments and has a value of about 150 dtex, and
    wherein said threads are twisted at a density of about 60–120 twists/meter.

2. Dental floss as claimed in claim 1, wherein said plurality of threads comprises 8 threads.

3. Dental floss as claimed in 1, wherein said POY filaments are made of polyester.

4. Dental floss as claimed in 1, wherein, the floss element comprises a wax coating of up to 10% of the thread weight.

5. Dental floss manufacturing method comprising the steps of
    assembling a series of POY polyester filaments to form a plurality of threads,
    texturizing said plurality of threads,
    forming a floss element by twisting together said threads at a density ranging between 60 and 120 twists/meter, and
    entangling said twisted threads without addition of binding agents,
    wherein said floss element comprises a total number of filaments ranging between 280 and 400, and
    wherein each of said plurality of threads comprises 47 filaments and has a value of about 150 dtex.

6. Dental floss, comprising:
    plural texturized threads cohesively twisted together and forming a floss element, each thread consisting of pre-oriented yarn filaments, wherein,
    the dental floss is free of any binding agents,
    the floss element is twisted at a density of from 60 to 120 twists/meter, and
    the floss element has a linear mass density value in a range from 1200 through 1400 dtex.

7. The floss of claim 6, wherein,
    eight threads twisted together form the floss element.

8. The floss of claim 7, wherein,
    the floss element is twisted at a density of 80 twists/meter.

9. The floss of claim 7, further comprising:
    a wax coating in an amount of 2–10% of the thread weight.

10. The floss of claim 6, wherein,
    the floss element comprises exactly 376 filaments.

11. The floss of claim 6, wherein,
the floss element comprises between 280 and 400 filaments.

12. The floss of claim 6, wherein,
the pre-oriented yarn filaments comprise polyester.

13. The floss of claim 6, wherein,
said floss element comprises a total number of filaments ranging between 280 and 400, and
wherein each of said plurality of threads has a value of about 150 dtex.

14. The floss of claim 6, wherein,
said floss element comprises a total number of filaments ranging between 280 and 400, and
wherein each of said plurality of threads has a value of about 150 dtex,
the number of texturized threads cohesively twisted together to form the floss element is in the range of 6 to 10.

\* \* \* \* \*